United States Patent [19]

Taniguchi et al.

[11] Patent Number: 4,978,789

[45] Date of Patent: Dec. 18, 1990

[54] PROCESS FOR PRODUCTION OF ALKENYL SUBSTITUTED AROMATIC COMPOUND

[76] Inventors: Katsuo Taniguchi, 68-3, Ushinoya-cho 3-chrome, Iwakuni-shi, Yamaguchi; Shigeki Fujikawa, 2-27, Seda 2-chrome, Waki-cho, Kuga-gun, Yamaguchi; Yoshito Kurano, 2-30, Kawanishi 3-chrome, Iwakuni-shi, Yamaguch, all of Japan

[21] Appl. No.: 376,929

[22] Filed: Jul. 10, 1989

Related U.S. Application Data

[63] Continuation of Ser. No. 871,546, Jun. 6, 1986, abandoned.

[30] Foreign Application Priority Data

Jun. 7, 1985 [JP] Japan .................................. 60-122557
Jun. 21, 1985 [JP] Japan .................................. 60-134293

[51] Int. Cl.$^5$ ..................... C07C 209/68; C07C 37/00
[52] U.S. Cl. ..................................... 564/305; 564/307; 564/308; 564/428; 568/731; 568/736; 568/740; 568/743; 568/766; 568/780; 568/781
[58] Field of Search ............... 564/305, 307, 308, 428; 568/716, 736, 740, 766, 780, 781, 731, 743

[56] References Cited

U.S. PATENT DOCUMENTS

| | | | |
|---|---|---|---|
| 3,418,381 | 12/1968 | Jennings et al. ...................... | 568/781 |
| 3,673,763 | 7/1972 | Dorfmann ............................. | 53/209 |
| 3,953,529 | 4/1976 | Yonemitsu et al. ................... | 568/743 |
| 4,028,340 | 8/1977 | Kanezaki . | |
| 4,346,249 | 8/1982 | Krabbenhoft ......................... | 568/781 |
| 4,503,271 | 3/1985 | Fujiwara et al. ..................... | 568/740 |

FOREIGN PATENT DOCUMENTS

| | | |
|---|---|---|
| 0128984 | 2/1983 | European Pat. Off. . |
| 1151457 | 1/1961 | Fed. Rep. of Germany . |
| 2304642 | 1/1973 | Fed. Rep. of Germany . |
| 0055529 | 5/1979 | Japan . |
| 0203022 | 12/1982 | Japan . |
| 0049328 | 3/1983 | Japan . |

*Primary Examiner*—Glennon H. Hollrah
*Attorney, Agent, or Firm*—Roylance, Abrams, Berdo & Goodman

[57] ABSTRACT

A process for producing an alkenyl substituted aromatic compound having the general formula (I):

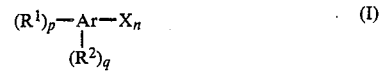

wherein Ar represents an aromatic ring, $R^1$ represents an alkenyl group having 2 to 8 carbon atoms, p is 1, 2, or 3 provided that $R^1$ may be the same or different when p is 2 or 3, $R^2$ represents an alkyl group having 1 to 8 carbon atoms, q is 0, 1, or 2 provided that $R^2$ may be the same or different when q is 2, X represents —OH or —$NR^3R^4$ wherein $R^3$ and $R^4$ independently represent hydrogen or an alkyl group having 1 to 2 carbon atoms, n is 1 or 2, provided that the sum of p and q is 1, 2, or 3 comprising the step of catalytically dehydrogenating an alkyl substituted aromatic compound having the general formula (III):

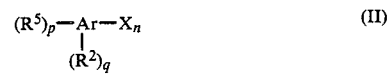

wherein $R^5$ represents an alkyl group having 2 to 8 carbon atoms and Ar, $R^2$, X, p, q, and n are the same as defined above, n is 1 or 2, provided that $R^5$ may be the same or different when p is 2 or 3 in the presence of a catalyst comprising (a) at least one iron oxide as a main component and (b) at least one oxide of metals belonging to the group III, IV or V of the periodic table of atoms.

This catalyst can produce an alkenyl substituted aromatic compound having a hydroxyl or amino group in the aromatic ring thereof from the dehydrogenation of the corresponding alkyl substituted aromatic compound at a high yield and high selectivity and has a prolonged catalyst life.

6 Claims, No Drawings

PROCESS FOR PRODUCTION OF ALKENYL SUBSTITUTED AROMATIC COMPOUND

This is a continuation of application Ser. No. 871,546, filed June 6, 1986, now abandoned.

BACKGROUND OF THE INVENTION

1. Field of the Invention

The present invention relates to a process for producing an alkenyl substituted aromatic compound having one or more hydroxyl or amino groups in the aromatic ring thereof from the catalytic dehydrogenation of an alkyl substituted aromatic compound. The resultant alkenyl substituted aromatic compounds are suitable for use as the starting materials for the production of, for example, agricultural chemicals (or pesticides), resin modifiers for epoxy resins, polyamide resins, polycarbonate resins and the like, and comonomers for various polymers.

2. Description of the Related Art

Various processes for producing alkenyl substituted aromatic compounds having a hydroxyl or amino group in the ring thereof are known in the art. For example, alkenyl substituted aromatic compounds having an amino group in the ring thereof, i.e., alkenyl substituted anilines, can be produced by cleaving hydroxyphenyl-aminophenyl-alkanes in the presence of a basic catalyst (see Japanese Examined Patent Publication (Kokoku) No. 41-1937). Alternatively, Annalen der Chemie 472, 11 (1929) discloses the production of alkenyl substituted anilines from the equi-molar reaction products of carbonyl compounds and aromatic amines. However, the yields of these methods are not good and it has not been proposed that alkenyl substituted anilines are obtained from a catalytic dehydrogenation of alkyl substituted anilines.

On the other hand, alkenyl substituted aromatic compounds having a hydroxyl group in the ring thereof, i.e., alkenyl substituted phenols, can be produced by dehydrating 2-hydroxy-2-propyl phenols in the presence of an acidic catalyst (see Journal of Organic Chemistry Vol. 23, 544 (1958)), but the yield of this method is not good. Alternatively, several methods have been proposed to produce alkenyl substituted phenols from the catalytic dehydrogenation of alkyl substituted phenols. For example, Japanese Examined Patent Publication (Kokoku) No. 53-43491 discloses the use of dehydrogenation catalysts composed of, as a main active component, an iron oxide or a combination thereof with an oxide of alkaline earth metal. However, this method involves problems in that the conversion of the starting material and the yield of the desired product are low. Japanese Unexamined Patent Publication (Kokai) Nos. 54-55529 and 55-154930 disclose the use of a dehydrogenation catalyst composed mainly of a chromium oxide. However, these methods involve problems in that the conversion of the starting materials is less than 40% and the yield of the desired product is also low. More particularly, the catalysts disclosed in Japanese Patent Kokai No. 54-55529 are composed of chromium oxides alone or a combination thereof with oxides of zinc, manganese, titanium, and/or zirconium. The activities of these catalysts are, however, low because the yields of the desired products are less than 40%. In addition, although this patent publication discloses, as a comparative example, the dehydrogenation of p-ethyl phenol with a commercially available catalyst composed of iron oxide, chromium oxide, and potassium oxide, the conversion and the selectivity of the desired product are even lower (i.e., conversion=11.5%, selectivity of p-ethenyl phenol=29.4%). The present inventors obtained a similar result from the dehydrogenation of alkyl phenols using a commercially available catalyst having the same components (i.e., a Nissan Girdler catalyst G64A composed of $Fe_2O_3$ (73.5%), $Cr_2O_3$ (1.9%), and $K_2CO_3$ (21.6%)) corresponding to the above-mentioned known catalyst, although the composition ratio of the metal oxides thereof is not clear. Thus, this type of catalyst cannot be practically used in the production of alkyl substituted phenols. The catalysts disclosed in Japanese Patent Kokai No. 55-154930 are composed of, as a main component, chromium oxide combined with metal oxides such as oxides of tin and iron. Although there are no specific disclosures as to the composition ratio of the catalyst in this specification, the chromium oxide-iron oxide catalyst used in Example 2 thereof is composed of about 50 parts by weight of the iron oxide based on 100 parts by weight of the chromium oxide. Such a catalyst containing, as a main component, the chromium oxide has a low activity and, therefore, is not suitable for use in the production of alkenyl substituted phenols from the practical point of view.

Furthermore, Japanese Unexamined Patent Publication No. 58-49328 discloses the production of ethenyl phenol from ethyl phenol using the oxides of barium and tin. This method, however, involves problems in that the conversion of the starting ethyl phenol and the yield of the desired ethenyl phenol are low.

However, as is well-known in the art, it is possible to change the catalyst activities when the composition ratio is varied, even when the constituents are the same. That is, it is possible to find a new catalyst having a higher activity compared to conventional catalysts by studying and appropriately modifying the known catalysts.

SUMMARY OF THE INVENTION

Accordingly, the objects of the present invention are to eliminate the above-mentioned problems of the conventional dehydrogenation catalysts and to provide a process for producing an alkenyl substituted aromatic compound having a hydroxyl or amino group in the aromatic ring thereof at a high yield and high selectivity.

Another object of the present invention is to provide a dehydrogenation catalyst having a prolonged life and suitable for use in the production of an alkenyl substituted aromatic compound having a hydroxyl or amino group in the aromatic ring thereof from the corresponding alkyl substituted aromatic compound at a high yield and selectivity.

Other objects and advantages of the present invention will be apparent from the following description.

In accordance with the present invention, there is provided a process for producing an alkenyl substituted aromatic compound having the general formula (I):

wherein Ar represents an aromatic ring, $R^1$ represents an alkenyl cycloalkenyl group having 2 to 8 carbon atoms, p is 1, 2, or 3 provided that $R^1$ may be the same or different when p is 2 or 3, $R^2$ represents an alkyl cycloalkyl group having 1 to 8 carbon atoms, q is 0, 1, or 2 provided that $R^2$ may be the same or different when q is 2, X represents —OH or —$NR^3R^4$ wherein $R^3$ and $R^4$ independently represent hydrogen or an alkyl group having 1 to 2 carbon atoms, n is 1 or 2, provided that the sum of p and q is 1, 2, or 3, comprising the step of catalytically dehydrogenating an alkyl substituted aromatic compound having the general formula (II):

wherein $R^5$ represents an alkyl cycloalkyl group having 2 to 8 carbon atoms, which is subjected to the catalytic dehydrogenation, and Ar, $R^2$, X, p, q, and n are the same as defined above, n is 1 or 2, provided that $R^5$ may be the same or different when p is 2 or 3, in the presence of a catalyst comprising (a) at least one iron oxide as a main component and (b) at least one oxide of metals belonging to the group III, IV, or V of the periodic table of atoms.

DESCRIPTION OF THE PREFERRED EMBODIMENTS

The dehydrogenation catalysts which can be used according to the present invention are those comprising (a) an iron oxide or a mixture of iron oxide as a main component and (b) one or more oxides of metals belonging to the groups III, IV, or V of the periodic table of atoms.

Amount of the iron of the iron oxide (a) in the catalyst according to the present invention is preferably 50 to 99, more preferably 60 to 90, in terms of the number of atoms, based on a total metal atom number of 100 in the catalyst. Amount of the metal of the metal oxide (b) in the present catalyst is preferably 0.1 to 40, more preferably 1 to 30, in terms of a number of atoms, based on a total metal atom number of 100 in the catalyst. It should be noted, however, that the ratio of the metal oxide (b) to the iron oxide (a) in the present catalyst is 0.001:1 to 1:1, preferably 0.01:1 to 1:1, more preferably 0.05:1 to 0.67:1, in terms of the ratio of the number of the metal atoms. When the ratio is within the above-mentioned range, the yield of the desired product is preferably improved.

The oxides of metals belonging to group III of the periodic table (i.e., "group III metals") which may be used according to the present invention includes, for example, the oxides of boron (B), aluminum (Al), gallium (Ga), indium (In), lanthanium (La), and cerium (Ce). Examples of the oxides of metals belonging to the group IV of the periodic table (i.e., "group IV metals") which may be used according to the present invention are the oxides of silicon (Si), titanium (Ti), germanium (Ge), zirconium (Zr), tin (Sn), hafnium (Hf), and lead (Pb). Examples of the oxides of metals belonging to the group V of the periodic table (i.e., "group V metals") which may be used according to the present invention are the oxides of vanadium (V), niobium (Nb), antimony (Sb), tantalum (Ta), and bismuth (Bi). These metal oxides may be used alone or in any combination thereof. Of these metal oxides, the oxides of the group IV metals, especially silicon oxide, zirconium oxide, titanium oxide, germanium oxide, or antimony oxide can be preferably used in the practice of the present invention.

According to the present invention, in addition to the above-mentioned essential constituents, the oxides of other metals such as those belonging to groups II and/or VI of the periodic table can be optionally incorporated into the catalyst in such an amount that 0.01 to 0.25, in terms of the number of the atoms, based on one atom of the iron of the iron oxide (a). Typical examples of such metal oxides are the oxides of calcium (Ca), magnesium (Mg), strontium (Sr), chromium (Cr), or molybdenum (Mo).

When chromium oxide is incorporated into the catalyst according to the present invention, the initial activity of the catalyst can be preferably maintained for a long time, that is, the life of the catalyst can be extended. Accordingly, it is preferable to incorporate chromium oxide into the catalyst in an amount of, for example, 0.01 to 0.25, more preferably 0.03 to 0.17, in terms of the ratio of the atom number of the metal to that of the iron (i.e., Cr/Fe).

Although the shapes or structures of iron oxides (a), the oxides of metals (b) belonging to group III, IV, or V of the periodic table of atoms and, as an optional component, the oxides of metals belonging to group II or IV of the periodic table in the present catalyst are not clear, it is believed that said metal oxides exist in the form of mixtures of the metal oxides themselves or the composite metal oxides in the catalysts. The metals in the metal oxides may be present in any atomic valencies thereof in the present catalyst. For example, in the case of the iron oxides, the valency of the iron may be II, III, or IV, in the case of the silicon oxides, the valency may be II or IV and, in the case of chromium oxide, the valency of chromium may be III or VI.

The dehydrogenation catalysts according to the present invention can be prepared in any conventional manner, for example, by baking or calcining mixtures of the iron compounds and the compounds of the group III, IV, and/or V metals and, optionally, other metal components such as the compounds of the group II and/or VI metals, all capable of being converted to metal oxides upon calcination at a certain temperature in an air atmosphere. Examples of such metallic compounds are inorganic compounds such as oxides, nitrates, hydrochlorides, and sulfates, organic compounds such as acetates and oxalates, organometallic compounds, metal hydroxides, and metal alcoxides. Typical examples of the metal compounds preferably used in the preparation of the catalysts according to the present invention are inorganic acid salts such as iron nitrates, silicon tetrachloride, sodium silicate, germanium nitrate, germanium chloride, zirconium nitrate, zirconium chloride, titanium chloride, titanyl nitrate, magnesium nitrate, magnesium chloride, magnesium sulfate, calcium nitrate, calcium chloride, chromium nitrate, chromium chloride, and potassium chromate cerium nitrate, cerium sulfate, and lanthanium nitrate; organic acid salts such as iron acetate, germanium acetate, magnesium acetate, and calcium oxalate; organometallic compounds such as methylmagnesium chloride, diethylchloro silane, and dibenzene chromium; metal hydroxides such as iron hydroxide, silicon hydroxide, titanium hydroxide, and magnesium hydroxide; and metallic alkoxides such as ethyl orthosilicate, t-butylalkoxy zirconium, and titanium tetrabutoxide.

The mixture of the above-mentioned metallic compounds can be prepared in any conventional manner. For example, an alkali is added to an aqueous solution of the above-mentioned mixed metal salts to form the hydroxides of the metals, an aqueous solution of the metallic salts is impregnated or supported on the other metal oxides, the metallic oxides are dipped in an aqueous solution of the metal salts, or the metal oxides or the metallic salts are mixed or kneaded together. Of these methods, a method in which an aqueous ammonia or an aqueous solution of an alkali metal is added to an aqueous solution of the mixed metallic salts is preferably used in the present invention.

According to the present invention, the abovementioned various type mixtures of the metallic compounds are baked or calcined at a temperature of, for example, 400° C. to 1000° C., preferably 500° C. to 700° C. The calcining time may be varied depending upon the calcining temperature but is generally 0.5 to 2 hours. The calcination is generally carried out in an air atmosphere, although it can be carried out under an inert atmosphere such as nitrogen.

According to the present invention, the abovementioned iron oxides (a), the oxides of metals (b), and the optional metal oxides may be supported on any conventional carriers. The catalyst in the present invention are generally used in any form (e.g., powders, spheres, tablets, cylindrical pellets, rings, and honeycombs).

The alkenyl substituted aromatic compounds having the general formula (I) (i.e., alkenyl substituted anilines or phenols) can be advantageously produced from the catalytic dehydrogenation of the alkyl substituted aromatic compounds having the general formula (II) (i.e., alkyl substituted anilines or phenols) in the presence of the above-mentioned catalysts.

The term "aromatic ring" herein used means a benzene ring or a naphthalene ring.

The alkyl substituted aromatic compounds having one or more, preferably one or two amino or hydroxyl groups in the ring thereof, are preferably those having one or more, preferably one to three alkyl groups with 2 to 8 carbon atoms, more preferably 2 to 6 carbon atoms such as ethyl, n-propyl, isopropyl, n-butyl, sec-butyl, isobutyl, n-amyl, iso-amyl, cyclohexyl, and cyclopentyl groups. Examples of the alkyl substituted aromatic compounds are alkyl substituted anilines having one or more alkyl groups such as ethyl aniline, N-methyl ethyl aniline, N,N'-dimethyl ethyl aniline, n-propyl aniline, m- or p-isopropyl aniline, n-butyl aniline, sec-butyl aniline, n-pentyl aniline, cyclopentyl aniline, cyclohexyl aniline, ethyl toluidine, ethyl xylidine, diethyl aniline, diisopropyl aniline, isopropyl toluidine, isopropyl xylidine, N-methyl isopropyl aniline, N,N'-dimethyl isopropyl aniline, ethyl phenylene diamine, and isopropyl phenylene diamine; and alkyl substituted phenols having one or more alkyl groups such as ethyl phenol, n-propyl phenol, m- or p-isopropyl phenol, n-butyl phenol, sec-butyl phenol, n-pentyl phenol, methyl (ethylphenol), methyl-n-propyl phenol, methyl isopropyl phenol, diethylphenol, isopropyl hydroquinone, dimethyl isopropyl phenol, ethyl naphthol, and isopropyl naphthol. Of these alkyl substituted aromatic compounds, those having $C_2$ to $C_4$ alkyl group such as o-ethyl aniline, m-ethyl aniline, p-ethyl aniline, m-isopropyl aniline, p-isopropyl aniline, m-n-propyl aniline and, p-n-propyl aniline; and o-ethyl phenol, m-ethyl phenol, p-ethyl phenol, m-isopropyl phenol, m-n-propyl phenol, and p-n-butyl phenol, are preferable.

The dehydrogenation reaction according to the present invention can be carried out under the conditions of, for example, a reaction temperature of 400° C. to 700° C., preferably 500° C. to 650° C., a reaction pressure of 0 to 10 kg/cm$^2$A, preferably 0 to 2 kg/cm$^2$A, and a feed rate of the starting material to the catalyst bed, i.e., liquid space velocity (i.e., LHSV) of 0.01 to 2.0, preferably 0.01 to 1.0, more preferably 0.07 to 0.8, although the scope of the present invention is by no means limited to these conditions. Furthermore, for the dehydrogenation reaction of the present invention, an inert gas such as nitrogen and/or a diluent such as water, steam, benzene, toluene, hexane, n-octane, and n-decane may be optionally used. When the diluent is used in the reaction, 3 to 50 moles, preferably 10 to 30 moles, based on one mole of the starting material, of the diluent can be preferably used. The use of the diluent preferably improves the selectivity of the desired alkenyl substituted aromatic compound and the catalyst life.

The dehydrogenation reaction according to the present invention may be carried out, generally, in any catalytic flow system. As the catalyst bed type, a fixed bed, moving bed, or fluidized bed may be used.

Typical examples of the alkenyl substituted aromatic compounds obtained by the present invention are alkenyl substituted anilines such as ethenyl aniline, m- or p-isopropenyl aniline, 1-propenyl aniline, 1-butenyl aniline, ethenyl toluidine, ethenyl xylidine, N-methyl ethenyl aniline, cyclopentenyl aniline, cyclohexenyl aniline, and ethenyl phenylene diamine; and alkenyl substituted phenols such as ethenyl phenol, m- or p-isopropenyl phenol, 1-propenyl phenol, 2-propenyl phenol, ethenyl naphthol, and isopropenyl phenol.

According to the present invention, the desired alkenyl substituted aromatic compounds can be advantageously prepared at a high yield and a high selectivity. Furthermore, the life of the catalyst can be prolonged.

EXAMPLES

The present invention now will be further illustrated by, but is by no means limited to, the following Examples and Comparative Examples, wherein all parts are parts by weight unless otherwise specified. The dehydrogenation reactions in the following Examples and Comparative Examples were all carried out at atmospheric pressure.

EXAMPLE 1

A 300 g amount of ferric nitrate (Fe(NO$_3$)$_3$.9H$_2$O) and 12.8 g of chromium nitrate (Cr(NO$_3$)$_3$.9H$_2$O) were dissolved in about 3 liters of distilled water and 20.6 g of 20% by weight silica sol, available from Nissan Chemical Ind., Ltd., was further added thereto. Then, 250 ml of commercially available about 25% aqueous ammonia was added at room temperature over 2 to 3 minutes while vigorously stirring The pH of the solution was 10.5. After the agitation was continued for a further 5 minutes, the resultant precipitates were recovered from the resultant dark brown slurry by repeated decantation and filtration. After washing, the cake thus obtained was dried at a temperature of about 90° C. for 20 hours in a dryer. The cake was then calcined at a temperature of 650° C. for 3 hours in an air atmosphere.

The composition of the composite oxide obtained above was Fe:Si:Cr=87:9:4 in terms of an atomic ratio percentage, as determined by atomic-absorption spectroscopy. The catalyst in the form of a mass was crushed and pulverized, followed by sifting to obtain catalyst particles having a mesh size of 20 to 32 (Tylor). A 20 ml amount of the catalyst particles was packed in a conventional quartz reaction tube having an inner diameter of 30 mm$\phi$.

The catalyst bed was set at a temperature of 560° C. and a mixture m-isopropyl aniline and water was quantitatively fed via a preheating and vaporizing mixer kept at a temperature of about 330° C. Thus, the mixture was passed through the catalyst bed. The feeding rate was such that the liquid space velocity (LHSV) of the m-isopropyl aniline was 0.3 hr$^{-1}$ and LHSV of the water was 0.4 hr$^{-1}$.

The reaction product was analyzed by a gas chromatography and the conversion of the starting m-isopropyl aniline and the selectivities of the products were obtained.

The results obtained from the steady reaction states after 5 hours of continuous reactions are shown in Table 1.

TABLE 1

| | |
|---|---|
| Conversion (mole %) of m-isopropyl aniline | 73.5 |
| Selectivity (mole %) of the products based on the starting material | |
| m-Isopropenyl aniline | 93.5 |
| m-Ethenyl aniline | 2.5 |
| m-Ethyl aniline | 2.0 |
| m,p-Toluidine | 0.4 |
| Others | 1.6 |

EXAMPLE 2

The metal oxide catalyst composed of Fe, Si, Ca, and Cr in the atomic ratio (%) of Fe:Si:Ca:Cr=84:8:4:4 was prepared in the same manner as in Example 1, except that calcium hydroxide powder was added to the preparation mixture after adding the silica sol.

The dehydrogenation reaction of 6-methyl-3-isopropyl aniline was carried out in the presence of the catalyst prepared above in the same manner as in Example 1 under the following conditions.

| | |
|---|---|
| Reaction temperature | 560° C. |
| LHSV of 6-methyl-3-isopropyl aniline | 0.3 hr$^{-1}$ |
| LHSV of water | 0.37 hr$^{-1}$ |

The results are shown in Table 2.

TABLE 2

| | |
|---|---|
| Conversion (mole %) of 6-methyl-3-isopropyl aniline | 71.2 |
| Selectivity (mole %) of the products based on the starting material | |
| 6-Methyl-3-isopropenyl aniline | 95.4 |
| 6-Methyl-3-ethenyl aniline | 2.4 |
| 6-Methyl-3-ethyl aniline | 1.5 |
| 2,5-Dimethyl aniline | 0.6 |
| Others | 1.1 |

EXAMPLE 3

A 303 g amount of ferric nitrate (Fe(NO$_3$)$_3$.9H$_2$O) and 19.2 g of chromium nitrate (Cr(NO$_3$)$_3$.9H$_2$O) were dissolved in about 4 liters of distilled water. Then, a commercially available about 25% by weight aqueous ammonia was added thereto, while stirring, until the pH of the solution became 10. After continuing the agitation for approximately 10 minutes, the resultant precipitates were filtered, followed by washing.

The resultant cake in the form of a gel was kneaded with 7 g of a commercially available bismuth oxide powder (Bi$_2$O$_3$) and 8.7 g of 20% by weight silica sol available from Nissan Chemical Ind., Ltd. for 30 minutes in a twin-screw ribbon type kneader. After drying the resultant product at a temperature of 90° C. as in Example 1, the dried product was then calcined at a temperature of 650° C. for 3 hours.

The composition of the resultant composite metal oxide was Fe:Bi:Cr:Si=83:7:6:4 in terms of an atomic ratio percentage.

The dehydrogenation reaction of p-ethyl aniline was carried out in the presence of the catalyst prepared above in the same manner as in Example 1 under the following conditions.

| | |
|---|---|
| Reaction temperature | 530° C. |
| LHSV of p-ethyl aniline | 0.4 hr$^{-1}$ |
| LHSV of water | 0.6 hr$^{-1}$ |

The results are shown in Table 3.

TABLE 3

| | |
|---|---|
| Conversion (mole %) of p-ethyl aniline | 68.8 |
| Selectivity (mole %) of the products based on the starting material | |
| p-Ethenyl aniline | 94.8 |
| p-Toluidine | 2.6 |
| Others | 2.6 |

COMPARATIVE EXAMPLE 1

The dehydrogenation reaction of m-isopropyl aniline was carried out in the same manner as in Example 1 under the following reaction conditions, except that a copper oxide-zinc oxide pellet catalyst (N-211) available from Nikki Chemical Co., Ltd. was packed in the reaction tube after sifting to a mesh size of 20 to 32.

| | |
|---|---|
| Reaction temperature | 560° C. |
| LHSV of m-isopropyl aniline | 0.3 hr$^{-1}$ |
| LHSV of water | 0.4 hr$^{-1}$ |

The results are shown in Table 4.

TABLE 4

| | |
|---|---|
| Conversion (mole %) of m-isopropyl aniline | 28.8 |
| Selectivity (mole %) of the products based on the starting material | |
| m-Isopropenyl aniline | 61.1 |
| m-Ethenyl aniline | 10.5 |
| m-Ethyl aniline | 4.9 |
| m,p-Toluidine | 7.5 |
| Aniline | 7.2 |
| Others | 8.8 |

EXAMPLE 4

A 303 g amount of ferric nitrate (Fe(NO$_3$)$_3$.9H$_2$O) and 12.8 g of chromium nitrate (Cr(NO$_3$)$_3$.9H$_2$O) were dissolved in about 3 liters of distilled water and 20.6 g of 20% by weight silica sol available from Nissan Chemical Ind., Ltd. was further added thereto. Then, 250 ml of a commercially available about 25% by weight aqueous ammonia was added at room temperature over 2 to 3 minutes while vigorously stirring. The pH of the solution was 10.5. After the agitation was continued for further 5 minutes, the resultant precipitates were recovered from the resultant brown slurry by repeated decantation and filtration. After washing, the cake thus obtained was dried at a temperature of about 90° C. for 20 hours in a dryer. The cake was then calcined at a temperature of 650° C. for 3 hours in an air atmosphere.

The composition of the composite metal oxide obtained above was Fe:Si:Cr=87:9:4 in terms of an atomic ratio percentage, as determined by atomic-absorption spectroscopy. The catalyst in the form of a mass was crushed and pulverized, followed by sifting to obtain the catalyst particles having a mesh size of 20 to 32 (Tylor). A 20 ml amount of the catalyst particles was packed in a conventional quartz reaction tube having an inner diameter of 30 mm$\phi$.

The catalyst bed was set at a temperature of 560° C. and a mixture of m-isopropyl phenol and water was quantitatively fed via a preheating and vaporizing mixer kept at temperature of about 330° C. Thus, the mixture was passed through the catalyst bed. The feeding rate was such that the LHSV of the m-isopropyl phenol was 0.3 hr$^{-1}$ and the LHV of the water was 0.4 hr$^{-1}$.

The reaction product was analyzed by gas chromatography and the conversion of the starting m-isopropyl phenol and the selectivities of the products were obtained.

The results obtained from the steady reaction states after 5 hours continuous reaction are shown in Table 5.

TABLE 5

| | |
|---|---|
| Conversion (mole %) of m-isopropyl phenol | 71.7 |
| Selectivity (mole %) of the products based on the starting material | |
| m-Isopropenyl phenol | 95.0 |
| m-Ethyl phenol | 1.2 |
| m-Ethenyl phenol | 0.9 |
| m,p-Cresol | 0.3 |
| Phenol | 0.4 |
| Others | 2.2 |

EXAMPLE 5

A 202 g amount of ferric nitrate (Fe(NO$_3$)$_3$.9H$_2$O) and 4.28 g of chromium nitrate (Cr(NO$_3$)$_3$.9H$_2$O) were dissolved in water to prepare 2 liters of the aqueous solution thereof. Then, 0.5 liters of an aqueous solution containing 5.03 g germanium oxide dissolved therein was added thereto and a 25% by weight aqueous ammonia was gradually added, while stirring, to adjust the pH of the aqueous mixture to 7. The precipitate thus formed was filtered and washed with water. The precipitate thus recovered was dried at a temperature of 90° C. for one day, and then calcined at a temperature of 700° C. for 3 hours. Thus, the desired Fe$_2$O$_3$.GeO$_2$.Cr$_2$O$_3$ catalyst was prepared. The composition of the composite metal oxide was Fe:Ge:Cr=88.8:9.1:2.1 in terms of the atomic ratio percentage. The catalyst in the form of a mass was crushed and pulverized to obtain the catalyst powder having a mesh size of 20 to 32 (Tylor). A 20 ml amount of the catalyst was packed in a conventional quartz reaction tube having an inner diameter of 25 mm. Then, m-ethyl phenol and water were allowed to react at a temperature of 560° C. in the reaction tube under the following conditions.

| | |
|---|---|
| Reaction temperature | 560° C. |
| LHSV | 0.8 hr$^{-1}$ |
| Water/ethyl phenol | 15 mol/mol |

The results are shown in Table 6.

TABLE 6

| | |
|---|---|
| Conversion (mole %) of m-ethyl phenol | 76.4 |
| Selectivities (mole %) of the products based on the starting material | |
| m-Ethenyl phenol | 94.7 |
| Cresols | 2.4 |
| Phenols | 1.3 |
| Others | 1.6 |

EXAMPLE 6

The composite metal oxide catalyst composed of Fe$_2$O$_3$.SiO$_2$.CaO.Cr$_2$O$_3$ in the atomic ratio (%) of Fe:Si:Ca:Cr=86:8:2:4 was prepared in the same manner as in Example 4, except that calcium hydroxide powder was added to the preparation mixture after adding the silica sol.

The dehydrogenation reaction of 6-methyl-3-isopropyl phenol was carried out in the presence of the catalyst prepared above in the same manner as in Example 4 under the following conditions.

| | |
|---|---|
| Reaction temperature | 560° C. |
| LHSV of 6-methyl-3-isopropyl phenol | 0.8 hr$^{-1}$ |
| Water:6-methyl-3-isopropyl phenol | 15:1 mol/mol |

The results are shown in Table 7.

TABLE 7

| | |
|---|---|
| Conversion (mole %) of 6-methyl-3-isopropyl phenol | 71.7 |
| Selectivity (mole %) of the products based on the starting material | |
| 6-Methyl-3-isopropenyl phenol | 94.5 |
| 6-Methyl-2-isopropenyl phenol | 2.4 |
| 6-Methyl-3-Ethenyl phenol | trace |
| Others | 3.1 |

EXAMPLE 7

The composite metal oxide of Fe$_2$O$_3$.ZrO$_2$.Cr$_2$O$_3$ was prepared in the same manner as in Example 4, except that 49.1 g of zirconyl nitrate (ZrO(NO$_3$)$_2$.2H$_2$O) was added in lieu of the silica sol. The atomic ratio of Fe:Zr:Cr was 78:18:4. The dehydrogenation of p-isopropyl phenol was carried out in the presence of the catalyst thus obtained in the same manner as in Example 4 under the following conditions.

| | |
|---|---|
| Reaction temperature | 560° C. |
| LHSV | 0.8 hr$^{-1}$ |
| Water/p-isopropyl phenol | 17 mol/mol |

The results are shown in Table 8.

TABLE 8

| | |
|---|---|
| Conversion (mole %) of p-isopropyl phenol | 77.5 |
| Selectivities (mole %) of the product based on the starting compound | |
| p-Isopropenyl phenol | 96.2 |
| p-Ethenyl phenol | 1.8 |
| p-Ethyl phenol | 1.7 |
| Others | 0.3 |

COMPARATIVE EXAMPLE 2

The dehydrogenation reaction of m-isopropyl phenol was carried out in the same manner as in Example 4 under the following reaction conditions, except that a catalyst G64A containing, as a main component, iron oxide available from Nissan Girdler Co., Ltd. was packed in the reaction tube after pulverizing and sifting to a mesh size of 20 to 32. The catalyst was composed of 73.5 wt % of $Fe_2O_3$, 1.9 wt % of $Cr_2O_3$, and 21.6 wt % of $K_2CO_3$.

| Reaction temperature | 560° C. |
|---|---|
| LHSV | 0.8 $hr^{-1}$ |
| Water/m-isopropyl phenol | 17 mol/mol |

The results are shown in Table 9.

TABLE 9

| | |
|---|---|
| Conversion (mole %) of m-isopropyl phenol | 27.2 |
| Selectivity (mole %) of the products based on the starting material | |
| m-Isopropenyl phenol | 73.5 |
| m-Ethyl phenol | 7.7 |
| Phenol | 12.1 |
| Aromatic hydrocarbons | 4.5 |
| Others | 2.2 |

COMPARATIVE EXAMPLE 3

A catalyst composed of iron oxide and chromium oxide was prepared in the same manner as in Example 4, except that no silica sol was added. The composition of the catalyst was Fe:Cr=94:6 in terms of the atomic ratio.

By using the catalyst prepared above, the dehydrogenation of m-isopropyl phenol was carried out in the same manner as in Example 4. As a result, the conversion of m-isopropyl phenol was 13 mole % and the selectivity of m-isopropenyl phenol was 67 mole %. Thus, the catalyst activity was low.

COMPARATIVE EXAMPLE 4

A catalyst composed of iron oxide and strontium having a ratio of Fe:Sr=92:8 in terms of an atomic ratio was prepared from ferric nitrate and strontium nitrate. The dehydrogenation reaction of m-isopropyl phenol was carried out by using the catalyst obtained above in the same manner as in Example 4.

The conversion of the isopropyl phenol was 26.9% and the selectivity of the m-isopropenyl phenol was 65%.

COMPARATIVE EXAMPLE 5

The dehydrogenation reaction of m-isopropyl phenol was carried out by using a catalyst composed of silicon oxide alone prepared from the silica sol available from Nissan Chemical Ind., Ltd. used in Example 4. The reaction conditions were as follows:

| Reaction temperature | 560° C. |
|---|---|
| LHSV | 0.8 $hr^{-1}$ |
| Water/isopropyl phenol | 15 mol/mol |

The results are shown in Table 10.

TABLE 10

| | |
|---|---|
| Conversion (mole %) of m-isopropyl phenol | 82 |
| Selectivity (mole %) of the products based on the starting material | |
| m-Isopropenyl phenol | 47 |
| Ethyl phenols | 22 |
| Ethenyl phenols | 17 |
| Cresols | 8 |

TABLE 10-continued

| | |
|---|---|
| Others | 6 |

COMPARATIVE EXAMPLE 6

The dehydrogenation reaction of m-ethyl phenol was carried out by using a zirconium oxide catalyst prepared from zirconyl nitrate under the following conditions.

| Reaction temperature | 560° C. |
|---|---|
| LHSV | 0.8 $hr^{-1}$ |
| Water/ethyl phenol | 11 mol/mol |

The results are shown in Table 11.

TABLE 11

| | |
|---|---|
| Conversion (mole %) of m-ethyl phenol | 22.5 |
| Selectivity (mole %) of the products based on the starting material | |
| m-Ethenyl phenol | 64.5 |
| Cresols | 24.2 |
| Others | 11.3 |

EXAMPLE 8

A 364 g amount of ferric nitrate $(Fe(NO_3)_3 \cdot 9H_2O)$ was dissolved in 3 liters of distilled water and 25 g of 20 wt % silica sol (i.e., $SiO_2$ content=about 20 wt %) available from Nissan Chemical Ind., Ltd. was further added. The mixture was thoroughly mixed. Then, 300 ml of a commercially available about 25% aqueous ammonia was instantaneously added to the resultant solution at room temperature, while vigorously stirring. The pH of the resultant solution was 10.2. The resultant precipitate was filtered and thoroughly washed and the resultant cake was dried at a temperature of 90° C. for 20 hours, followed by calcining at a temperature of 650° C. for 3 hours in an air atmosphere.

The composition of the resultant metal oxide was determined by atomic-absorption spectroscopy. The atomic ratio of Fe:Si was 91:9. The dehydrogenation of m-isopropyl phenol was carried out by using the resultant catalyst under the following conditions in the same manner as in Example 4.

| Reaction temperature | 560° C. |
|---|---|
| LHSV | 0.7 $hr^{-1}$ |
| Water/m-isopropyl phenol | 15 mol/mol |

The results are shown in Table 12.

TABLE 12

| | |
|---|---|
| Conversion (mole %) of m-isopropyl phenol | 68.5 |
| Selectivity (mole %) of the products based on the starting material | |
| m-Isopropenyl phenol | 93.6 |
| Ethyl phenols | 1.5 |
| Ethenyl phenols | 1.7 |
| Cresol | 0.4 |
| Phenol | 0.4 |
| Others | 2.4 |

EXAMPLE 9

The dehydrogenation of m-isopropenyl aniline was carried out by using the catalyst used in Example 8 in the same manner as in Example 1. The results are shown in Table 13.

TABLE 13

| | |
|---|---|
| Conversion (mole %) of m-isopropyl aniline | 69.0 |
| Selectivity (mole %) of the products based on the starting material | |
| m-Isopropenyl aniline | 93.1 |
| m-Ethenyl aniline | 1.7 |
| m-Ethyl aniline | 1.5 |
| m,p-Toluidine | 0.9 |
| Others | 2.8 |

EXAMPLE 10

A 365 g amount of ferric nitrate ($Fe(NO_3)_3.9H_2O$) was dissolved in about 3 liters of distilled water and 100 ml of commercially available titanium trioxide solution (about 20% aqueous hydrochloric solution available from Wako Junyaku Co., Ltd.) was then added. After obtaining a homogeneous solution, 330 ml of commercially available about 25 wt % aqueous ammonia was instantaneously added thereto, while vigorously stirring. The resultant dark brown precipitates were filtered and washed repeatedly until no chlorine ions could be detected in the filtrate. The precipitates thus recovered were dried at a temperature of 90° C. for 20 hours, followed by calcining at a temperature of 600° C. for 3 hours in the air. Thus, the composite metal oxide composed of iron and titanium was obtained. The composition of the composite metal oxide was Fe:Ti=88:12 in terms of an atomic ratio.

The dehydrogenation of m-isopropenyl phenol was carried out by using the catalyst obtained above under the following conditions in the same manner as in Example 4.

| | |
|---|---|
| Reaction temperature | 560° C. |
| LHSV | 0.8 hr$^{-1}$ |
| Water/isopropyl phenol | 15 mol/mol |

The results are shown in Table 14.

TABLE 14

| | |
|---|---|
| Conversion (mole %) of m-isopropyl phenol | 67.0 |
| Selectivity (mole %) of the products based on the starting material | |
| m-Isopropenyl phenol | 93.5 |
| Ethyl phenol | 1.2 |
| Ethenyl phenol | 1.0 |
| Cresols | 0.4 |
| Phenol | 0.7 |
| Others | 3.2 |

EXAMPLE 11

The dehydrogenation reaction of m-isopropyl aniline was carried out in the same manner as in Example 1 by using the catalyst used in Example 10.

The results are as shown in Table 15.

TABLE 15

| | |
|---|---|
| Conversion (mole %) of m-isopropyl aniline | 72.2 |
| Selectivity (mole %) of the products based on the starting material | |
| m-Isopropenyl aniline | 95.2 |
| Ethenyl anilines | 2.0 |
| Ethyl anilines | 1.7 |
| m,p-Toluidine | 0.4 |
| Others | 0.7 |

EXAMPLE 12

A 365 g amount of ferric nitrate ($Fe(NO_3)_3.9H_2O$) was dissolved in about 3 liters of distilled water and an aqueous solution of 42 g indium trichloride.tetra hydrates available from Wako Junyaku Co., Ltd. dissolved in 200 ml of distilled water was further added thereto. Then, 330 ml of a commercially available about 25 wt % aqueous ammonia was instantaneously added thereto, while vigorously stirring. The resultant dark brown precipitates were filtered and washed repeatedly with water until no chlorine ion could be detected in the filtrate. Thereafter, the cake thus obtained was dried at a temperature of about 90° C. for 20 hours, followed by calcining at a temperature of 600° C. for 3 hours in an air atmosphere.

The composition of the composite oxide obtained above was Fe:In=93:7 in terms of an atomic ratio. The dehydrogenation reaction of m-isopropyl phenol was carried out by using the catalyst obtained above under the following conditions in the same manner as in Example 4.

| | |
|---|---|
| Reaction temperature | 560° C. |
| LHSV | 0.8 hr$^{-1}$ |
| Water/isopropyl phenol | 15 mol/mol |

The results are shown in Table 16.

TABLE 16

| | |
|---|---|
| Conversion (mole %) of m-isopropyl phenol | 68.0 |
| Selectivity (mole %) of the products based on the starting material | |
| m-Isopropenyl phenol | 93.6 |
| Ethyl phenols | 1.2 |
| Ethenyl phenols | 1.3 |
| Cresols | 0.4 |
| Phenol | 0.7 |
| Others | 2.8 |

EXAMPLE 13

The dehydrogenation reaction of p-isopropyl aniline was carried out by using the catalyst used in Example 12 in the same manner as in Example 1.

The results are shown in Table 17.

TABLE 17

| | |
|---|---|
| Conversion (mole %) of p-isopropyl aniline | 67.5 |
| Selectivity (mole %) of the products based on the starting material | |
| p-Isopropenyl aniline | 92.6 |
| Ethenyl anilines | 2.5 |
| Ethyl anilines | 1.6 |
| m,p-Toluidine | 0.8 |
| Aniline | 0.2 |
| Others | 2.1 |

EXAMPLE 14

A 163 g amount of a commercially available anhydrous ferric chloride and 18 g of vanadium oxytrichloride were dissolved in a hydrochloric aqueous solution. To the resultant solution, a commercially available 25 wt % aqueous ammonia was added, while vigorously stirring until the pH of the solution became 9.5 or more. The resultant precipitate was washed repeatedly with water until no chlorine ion could be detected in the filtrate. Thereafter the precipitate was dried and then calcined at a temperature of 600° C. Thus, the composite metal oxide containing Fe and V in an atomic ratio of Fe:V=92.8 was obtained.

The dehydrogenation reaction of m-isopropyl phenol was carried out by using the catalyst obtained above under the following conditions in the same manner as in Example 4.

| Reaction temperature | 560° C. |
|---|---|
| LHSV | 0.8 hr$^{-1}$ |
| Water/isopropyl phenol | 15 mol/mol |

The results are shown in Table 18.

TABLE 18

| | |
|---|---|
| Conversion (mole %) of m-isopropyl phenol | 66.9 |
| Selectivity (mole %) of the products based on the starting material | |
| m-Isopropenyl phenol | 92.2 |
| Ethyl phenols | 1.2 |
| Ethenyl phenols | 1.6 |
| Cresols | 0.7 |
| Phenol | 0.7 |
| Others | 3.6 |

EXAMPLE 15

The dehydrogenation reaction of m-isopropyl aniline was carried out by using the catalyst used in Example 14 in the same manner as in Example 1 under the following conditions:

| Reaction temperature | 560° C. |
|---|---|
| LHSV (m-isopropyl aniline) | 0.3 hr$^{-1}$ |
| LHSV (water) | 0.4 hr$^{-1}$ |

The results are shown in Table 19.

TABLE 19

| | |
|---|---|
| Conversion (mole %) of m-isopropyl aniline | 65.3 |
| Selectivity (mole %) of the products based on the starting material | |
| m-Isopropenyl aniline | 92.1 |
| Ethyl aniline | 2.1 |
| Ethenyl aniline | 2.6 |
| m,p-Toluidine | 1.0 |
| Aniline | 0.2 |
| Others | 2.3 |

EXAMPLE 16

The dehydrogenation reaction of p-isopropyl aniline was carried out by using the catalyst used in Example 8 in the same manner as in Example 1, under the following conditions:

| Reaction temperature | 560° C. |
|---|---|
| LHSV (p-isopropyl aniline) | 0.3 hr$^{-1}$ |
| LHSV (water) | 0.4 hr$^{-1}$ |

The results are shown in Table 20.

TABLE 20

| | |
|---|---|
| Conversion (mole %) of p-isopropyl aniline | 73.0 |
| Selectivity (mole %) of the products | |
| p-Isopropenyl aniline | 90.3 |
| p-Ethenyl aniline | 3.5 |
| p-Ethyl aniline | 2.7 |
| m,p-Toluidine | 1.0 |
| Aniline | 0.2 |
| Others | 2.3 |

We claim:

1. A process for producing an alkenyl substituted aromatic compound having the general formula (I):

wherein Ar represents an aromatic ring, R, represents an alkenyl group having 2 to 8 carbon atoms, p is 1, 2, or 3 provided that $R^1$ may be the same or different when p is 2 or 3, $R^2$ represents an alkyl group having 1 to 8 carbon atoms or a cyclocalkyl group having 3 to 8 carbon atoms, q is 0, 1, or 2 provided that $R^2$ may be the same or different when q is 2, X represents —OH or —NR$^3$R$^4$ wherein $R^3$ and $R^4$ independently represent hydrogen or an alkyl group having 1 to 2 carbon atoms, n is 1 or 2, provided that the sum of p and q is 1, 2 or 3, comprising the step of catalytically dehydrogenating an alkyl substituted aromatic compound having the general formula (II):

wherein $R^5$ represents an alkyl group having 2 to 8 carbon atoms, and Ar, $R^2$, X, p, q, and n are the same as defined above, n is 1 or 2, provided that $R^5$ may be the same or different when p is 2 or 3 in the presence of a catalyst comprising (a) at least one iron oxide, as a main component, and (b) at least one silicon oxide.

2. A process as claimed in claim 1, wherein the ratio of the silicon oxide (b) to the iron oxide (a) in the catalyst is 0.001:1 to 1:1, in terms of the ratio of the number of the metal atoms.

3. A process as claimed in claim 1, wherein the alkyl substituted aromatic compound is an alkyl substituted aniline.

4. A process as claimed in claim 1, wherein the alkyl substituted aromatic compound is an alkyl substituted phenol.

5. A process as claimed in claim 1, wherein the catalyst further comprises (c) chromium oxide, calcium oxide, or the mixture thereof.

6. A process as claimed in claim 1, wherein the alkenyl compound having the formula (I) is formula:

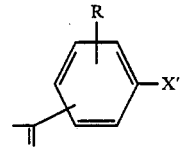

wherein R represents H, CH$_3$ or C$_2$H$_5$ an and the alkyl substituted aromatic compound having the formula (II) is represented by the formula:

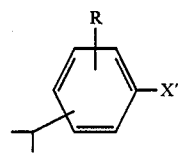

wherein R and X, are as defined above.

* * * * *

UNITED STATES PATENT AND TRADEMARK OFFICE
CERTIFICATE OF CORRECTION

PATENT NO. : 4,978,789

DATED : December 18, 1990

INVENTOR(S) : Taniguchi et al

It is certified that error appears in the above-identified patent and that said Letters Patent is hereby corrected as shown below:

Title page, column 2, lines 1 and 2, "Attorney, Agent, or Firm - Roylance, Abrams, Berdo & Goodman" should read -- Cushman, Darby & Cushman --

Signed and Sealed this

Twentieth Day of August, 1991

*Attest:*

HARRY F. MANBECK. JR.

*Attesting Officer*     *Commissioner of Patents and Trademarks*